(12) United States Patent
Yang et al.

(10) Patent No.: US 6,669,904 B1
(45) Date of Patent: Dec. 30, 2003

(54) STABILIZED BROMINE SOLUTIONS, METHOD OF MAKING AND USES THEREOF FOR BIOFOULING CONTROL

(75) Inventors: Shunong Yang, Naperville, IL (US); Donald A. Johnson, Batavia, IL (US); Robert L. Wetegrove, Winfield, IL (US); George J. Collias, River Forest, IL (US)

(73) Assignee: Ondeo Nalco Company, Naperville, IL (US)

( * ) Notice: Subject to any disclaimer, the term of this patent is extended or adjusted under 35 U.S.C. 154(b) by 0 days.

(21) Appl. No.: 09/920,399

(22) Filed: Aug. 1, 2001

Related U.S. Application Data

(63) Continuation-in-part of application No. 09/283,122, filed on Mar. 31, 1999, now Pat. No. 6,270,722.

(51) Int. Cl.[7] .............................. A61L 2/18; C01B 7/09
(52) U.S. Cl. .............................. 422/37; 422/7; 422/14; 423/500; 252/186.36; 252/187.2; 210/754; 162/70
(58) Field of Search .................. 422/37, 7, 14; 423/462, 500; 210/754; 252/186.36, 187.2; 162/70

(56) References Cited

U.S. PATENT DOCUMENTS

| | | | |
|---|---|---|---|
| 3,328,294 A | 6/1967 | Self et al. | |
| 3,558,503 A | 1/1971 | Goodenough et al. | |
| 3,767,586 A | 10/1973 | Rutkiewic et al. | |
| 5,264,136 A | * 11/1993 | Howarth et al. | 210/754 |
| 5,565,109 A | * 10/1996 | Sweeny | 210/755 |
| 5,683,654 A | 11/1997 | Dallmier et al. | |
| 5,795,487 A | 8/1998 | Dallmier et al. | |
| 6,007,726 A | 12/1999 | Yang et al. | |
| 6,015,782 A | 1/2000 | Petri et al. | |
| 6,110,387 A | 8/2000 | Choudhury et al. | |
| 6,478,972 B1 | 11/2002 | Shim et al. | 422/37 X |
| 2002/0056689 A1 | 5/2002 | Shim et al. | |

FOREIGN PATENT DOCUMENTS

| | | |
|---|---|---|
| WO | WO 97/20909 | 6/1997 |
| WO | WO-9720909 A1 * | 6/1997 |
| WO | WO 97/43392 | 11/1997 |

* cited by examiner

*Primary Examiner*—Elizabeth McKane
(74) *Attorney, Agent, or Firm*—Michael B. Martin; Thomas M. Breininger

(57) ABSTRACT

Stabilized bromine solutions are prepared by combining a bromine source and a stabilizer to form a mixture, and then adding an oxidizer to the mixture.

20 Claims, No Drawings

STABILIZED BROMINE SOLUTIONS, METHOD OF MAKING AND USES THEREOF FOR BIOFOULING CONTROL

REFERENCE TO RELATED PATENT

This application is a continuation-in-part of U.S. Ser. No. 09/283,122, filed on Mar. 31, 1999 now U.S. Pat. No. 6,270,722.

FIELD OF THE INVENTION

This invention relates generally to water treatment and, more particularly, to stabilized bromine solutions, method of making and uses thereof for biofouling control.

BACKGROUND OF THE INVENTION

Sodium hypochlorite has been widely used in a variety of industrial and recreational water systems to control biofouling. However, sodium hypochlorite is unstable and must be provided in a stabilized form. There are several methods known in the art for stabilizing hypochlorite (See, e.g., U.S. Pat. Nos. 3,328,294 and 3,767,586).

Bromine is preferred over chlorine for use in water treatment because of its lower volatility and better performance at high pH and amine environments. However, like sodium hypochlorite, sodium hypobromite is unstable in typical storage conditions and must therefore also be provided in a stabilized form. U.S. Pat. Nos. 5,683,654 and 5,795,487, as well as the references disclosed therein, teach various methods for stabilizing sodium hypobromite. The '654 and '487 patents disclose batch methods which utilize sodium hypochlorite and sodium bromide as starting materials, followed by the addition of a stabilizer. WO 97/20909 similarly discloses a process which includes a hypobromite formation step followed by a bromine stabilization step. However, a disadvantage associated with this technique is that unstabilized hypobromite is formed in a separate step at a high concentration and pH. It is known that unstabilized hypobromite degrades quickly under such conditions to form bromate, a non-biocidal compound that is very toxic and a suspected carcinogen.

In addition, WO 97/43392 discloses a process that first forms stabilized chlorine compounds and then converts them to stabilized bromine compounds. However, this type of process is limiting because only hypochlorite-releasing compounds can be used as the oxidizing source.

Therefore, because the demand for stabilized bromine solutions is expected to increase in the future due to its advantages over chlorine, there is a need for other cost-effective methods of making stabilized bromine which can use a wider range of oxidants.

Accordingly, it would be desirable to provide a method of making a stabilized bromine solution which can be carried out as a batch or continuous process right at the site of the commercial application. It would also be desirable to develop a method of making a stabilized bromine solution which is flexible and allows a variety of oxidizers to be utilized.

SUMMARY OF THE INVENTION

The stabilized bromine solutions of the present invention are prepared by combining a bromine source and a stabilizer to form a mixture, and then adding an oxidizer to the mixture.

The inventive method is economically appealing because it can be carried out as a batch or continuous process at the commercial application site, thereby eliminating the need to store and transport the stabilized bromine solutions. The method of preparation is also flexible and allows for the utilization of a variety of oxidizers.

DETAILED DESCRIPTION OF THE INVENTION

The present invention is directed to a method of making stabilized bromine solutions. In accordance with this invention, a bromine source and a stabilizer are combined to form a mixture, and then an oxidizer is added to the mixture.

The bromine sources which may be used in the practice of the present invention include hydrobromic acid, and alkali or alkaline earth metal bromides, such as sodium bromide, potassium bromide and lithium bromide.

The stabilizers which may be employed in this invention have the chemical formula $R-NH-R^1$, wherein R and $R^1$ are selected from the group consisting of $R^2CO$, $R^2SO_2$, $R^2CF_2$, $R^2CHF$, H, OH and $PO(OH)_2$, and $R^2$ is an alkyl group or an aromatic group. Suitable stabilizers include saccharin, urea, thiourea, creatinine, cyanuric acids, alkyl hydantoins, monoethanolamine, diethanolamine, organic sulfonamides, biuret, sulfamic acid and its alkali or alkaline earth metal salts, organic sulfamates and melamine. Sulfamic acid and its alkali or alkaline earth metal salts are the most preferred stabilizers.

Optionally, other water treatment chemicals, such as tracing compounds, surfactants, corrosion inhibitors and scale inhibitors, can be added to the bromine/stabilizer mixture.

The oxidizers which may be used include chlorine gas, hypochlorous acid, hypochlorite salt, chlorite, chlorate, elemental bromine, bromine chloride, hydrogen peroxide, persulfate, pernanganate and peracetic acid. Chlorine gas, hypochlorous acid and hypochlorite salt are the most preferred oxidizers. It is believed that other peroxy compounds can also be used in accordance with this invention.

The stabilized bromine solutions which are prepared in accordance with this invention can be prepared at the site of the commercial application. This eliminates the need to store and transport the stabilized bromine solutions and thus the need for adding caustic to adjust the pH and extend the shelf life of the solutions. The present invention can be carried out as either a batch or continuous process.

It is preferred that the molar ratio between the bromine source and the stabilizer be in the range of about 0.1 to 10. The molar ratio between the bromine source and the oxidizer should preferably be in the range of about 0.2 to 5.

The stabilized bromine solutions which are prepared in accordance with this invention may be used in a wide variety of commercial applications. These applications include, but are not limited to, the use of the stabilized bromine solution: (1) as the bleaching agent in a method for the laundering of soiled garments in which the soiled garments are washed in an aqueous media containing a detergent and a bleaching agent; (2) as the oxidizing agent in a method for the manufacture of cellulosic materials in which cellulosic fibers are bleached; (3) as the oxidizing and biocidal agent in a method for the control of biofouling in a recreational water system in which an oxidizing and biocidal agent is added to control biofouling; (4) as the oxidizing and biocidal agent in a method for the control of biofouling on a hard surface in which an oxidizing and biocidal agent is applied to the surface to control biofouling on the surface; (5) in a method for the control of biofouling occurring on the surfaces of equipment in contact with produced oil field waters; (6) in a method for controlling biofouling in an aqueous system; (7) in a method for controlling biofouling in pulp and paper manufacturing process water and process chemicals; and (8) in a method for controlling microbial growth in an aqueous stream used for transporting or processing food products and on food surfaces and equipment surfaces that come in contact with the aqueous stream.

In another embodiment, the invention is a method of preventing biofouling on the surfaces of equipment in contact with an industrial water system. The method comprises adding an effective biofouling controlling amount of a stabilized bromine solution to the water system, wherein the solution is prepared by combining a bromine source and a stabilizer to form a mixture, and then adding an oxidizer to the mixture.

The types of industrial water systems in which the stabilized bromine solution may be used to prevent biofouling include, but are not limited to, cooling water systems, sweetwater systems, gas scrubber systems, air washer systems, evaporative condensers, pasteurizers, produce sanitizer streams, fire protection water systems and heat exchanger tubes.

It is preferred that the amount of stabilized bromine solution which is added to the industrial water system be in the range of about 0.1 ppm to about 2000 ppm and preferably in the range of about 0.5 ppm to about 500 ppm, based on available chlorine concentration. The stabilized bromine solution can be added to the water system by any conventional method, i.e., by slug, intermittently or continuously.

EXAMPLES

The following examples are intended to be illustrative of the present invention and to teach one of ordinary skill how to make and use the invention. These examples are not intended to limit the invention or its protection in any way.

Example 1

This example demonstrates the impact of caustic addition. It also illustrates that caustic addition is not needed if the inventive stabilized bromine solutions are prepared and used at the site of the commercial application.

Three stabilized bromine formulations were prepared with the only difference being their caustic contents. The formulations underwent an accelerated thermal degradation test at 135° F. and the product actives were determined by potassium-thiosulfate titration at various times. The half lives of the products were calculated from first order decay curves. As shown below in Table 1, the product half lives indicate that the lower the caustic addition, the shorter the shelf life.

TABLE 1

| Raw material | Formulation (moles) | | |
|---|---|---|---|
| | A | B | C |
| Sodium hydroxide | 0.176 | 0.628 | 5.808 |
| Sulfamic acid | 0.126 | 0.126 | 0.126 |
| Water | 0.488 | 0.488 | 0.488 |
| Sodium hypochlorite | 0.09 | 0.09 | 0.09 |
| Sodium bromide | 0.09 | 0.09 | 0.09 |
| Product half life (days) | 1.8 | 41.3 | 41.3 |

Example 2

A laboratory experiment was conducted at room temperature (70° F.) by:
1. Preparing a mixture (solution A) of sodium bromide and sodium sulfamate to contain 33.3% wt of sodium bromide and 17.4% of sodium sulfamate in water;
2. Adding 0.76 ml of 10.9% wt (as available chlorine) chlorine bleach to 1000 ml of synthetic cooling water containing 225 ppm (as $CaCO_3$) hardness and 125 ppm (as $CaCO_3$) total alkalinity (solution B); and
3. Adding 0.241 ml of solution A to solution B to form the final solution.

One milliliter of the final solution was taken at different time points and diluted 100 times in deionized water. The halogen residual concentrations in the diluted solution were determined using Hach's DPD method 80 on a DR-2000 spectrophotometer. Three types of DPD measurements were taken: (1) free halogen residual using free chlorine reagent and read at 20 seconds after the reagent was added to the test solution, (2) total halogen residual using total chlorine reagent, and (3) 3-minute halogen residual using free chlorine reagent and read at 3 minutes after the reagent was added. As discovered by the inventors, the difference between the total halogen residual and 3-minute halogen residual is the concentration of N-chlorosulfamate.

While determining the halogen residual in the solution, another one milliliter of the final solution was taken and added to a flask containing 100 ml of the synthetic cooling water with $2.4 \times 10^6$ CFU/ml of cooling water mixed culture bacteria. After five minutes of mixing, an aliquot of sample was taken from the flask and neutralized with sodium bisulfite. The surviving bacterial population was enumerated on 3M's aerobic count Petrifilm® media after appropriate dilution. The test results are summarized below in Table 2.

TABLE 2

| | Halogen residual concentration (ppm as avail. $Cl_2$) | | | |
|---|---|---|---|---|
| Time (minutes) | Free halogen | 3-minute free | Total halogen | log reduction of bacterial count |
| 10 | 0.56 | 0.56 | 0.92 | >6.3 |
| 30 | 0.48 | 0.60 | 0.91 | >6.3 |
| 66 | 0.57 | 0.66 | 0.93 | >6.3 |
| 135 | 0.63 | 0.70 | 0.93 | >6.3 |
| 180 | 0.63 | 0.76 | 0.95 | >6.3 |

The results show the effective biocidal performance of the prepared solution. In addition, the solution was found to be stable and there was no reduction of total halogen residual during the test period while the concentration of N-chlorosulfamate decreased with an increase in the N-bromosulfamate concentration.

While the present invention is described above in connection with preferred or illustrative embodiments, these embodiments are not intended to be exhaustive or limiting of the invention. Rather, the invention is intended to cover all alternatives, modifications and equivalents included within its spirit and scope, as defined by the appended claims.

What is claimed is:

1. A method of making a stabilized bromine solution comprising the steps of:
   a. combining a bromine source and a stabilizer to form a mixture; and
   b. adding an oxidizer to the mixture, wherein the oxidizer is selected from the group consisting of chlorine gas, hypochlorous acid and hypochlorite salt.

2. The method of claim 1 wherein the bromine source is selected from the group consisting of hydrobromic acid, alkali earth metal bromides and alkaline earth metal bromides.

3. The method of claim 1 wherein the stabilizer has the chemical formula R—NH—$R^1$, wherein R and $R^1$ are selected from the group consisting of $R^2CO$, $R^2SO_2$, $R^2CF_2$, $R^2CHF$, H, OH and $PO(OH)_2$, and $R^2$ is an alkyl group or an aromatic group.

4. The method of claim 1 wherein the stabilizer is selected from the group consisting of saccharin, urea, thiourea, creatinine, cyanuric acids, alkyl hydantoins, monoctumnolamine, diethanolamine, organic sulfonamides, biuret, sulfamic acid and its alkali or alkaline earth metal salts, organic sulfamates and melamine.

5. The method of claim 1 wherein the stabilizer is selected from the group consisting of sulfamic acid and its alkali or alkaline earth metal salts.

6. The method of claim 1 wherein the molar ratio between the bromine source and the stabilizer is in the range of about 0.1 to 10.

7. The method of claim 1 wherein the molar ratio between the bromine source and the oxidizer is in the range of about 0.2 to 5.

8. A stabilized bromine solution produced by the method of claim 1.

9. In a method for the laundering of soiled garments in which the soiled garments are washed in an aqucous media containing a detergent and a bleaching agent, the improvement comprising using as the bleaching agent the stabilized bromine solution of claim 8.

10. In a method for the manufacture of cellulosic materials in which cellulosic fibers are bleached with an oxidizing agent, the improvement comprising using as the oxidizing agent the stabilized bromine solution of claim 8.

11. In a method for the control of biofouling in a recreational water system in which an oxidizing and biocidal agent is added to control biofouling, the improvement comprising using as the oxidizing and biocidal agent the stabilized bromine solution of claim 8.

12. In a method for the control of biofouling on a hard surface in which an oxidizing and biocidal agent is applied to the surface to control biofouling on the surface, the improvement comprising using as the oxidizing and biocidal agent the stabilized bromine solution of claim 8.

13. In a method for the control of biofouling occurring on the surfaces of equipment in contact with produced oil field waters, the improvement comprising adding to the produced oil field waters an effective biofouling controlling amount of the stabilized bromine solution of claim 8.

14. A method of controlling biofouling in an aqueous system which comprises adding to the aqueous system an effective, biofouling controlling amount of the stabilized bromine solution of claim 8.

15. A method of controlling biofouling in pulp and paper manufacturing process water and process chemicals which comprises adding to the process water an effective, biofouling controlling amount of the stabilized bromine solution of claim 8.

16. A method of controlling microbial growth in an aqueous stream used for transporting or processing food products and on food surfaces and equipment surfaces that come in contact with the aqueous stream which comprises adding to the aqueous stream an effective, microbial growth controlling amount of the stabilized bromine solution of claim 8.

17. A method of preventing biofouling on the surfaces of equipment in contact with an industrial water system which comprises adding to the water system an effective biofouling controlling amount of a stabilized bromine solution, said solution having been prepared by the steps of:

a. combining a bromine source and a stabilizer to form a mixture; and b. adding an oxidizer to the mixture, wherein the oxidizer is selected from the group consisting of chlorine gas, hypochlorous acid and hypochlorite salt.

18. The method of claim 17 wherein the industrial water system is selected from the group consisting of a cooling water system, sweetwater system, gas scrubber system, air washer system evaporative condenser, pasteurizer, produce sanitizer stream, fire protection water system and heat exchanger tube.

19. The method of claim 17 wherein the stabilized bromine solution is added to the industrial water system in an amount of from about 0.1 to about 2000 ppm as available chlorine.

20. The method of claim 17 wherein the stabilized bromine solution is added to the industrial water system in an amount of from about 0.5 to about 500 ppm as available chlorine.

\* \* \* \* \*